United States Patent

Cudahy et al.

Patent Number: 5,184,620
Date of Patent: Feb. 9, 1993

[54] METHOD OF USING A MULTIPLE ELECTRODE PAD ASSEMBLY

[75] Inventors: Michael J. Cudahy, Milwaukee, Wis.; Robert A. Stratbucker, Omaha, Nebr.

[73] Assignee: Marquette Electronics, Inc., Milwaukee, Wis.

[21] Appl. No.: 813,473

[22] Filed: Dec. 26, 1991

[51] Int. Cl.$^5$ .......................... A61B 5/0402
[52] U.S. Cl. ..................... 128/639; 128/419 P; 128/419 D; 128/798; 128/696
[58] Field of Search ............. 128/419 D, 419 P, 639, 128/644, 695, 696, 798, 799

[56] References Cited

U.S. PATENT DOCUMENTS

| | | | |
|---|---|---|---|
| 2,943,628 | 7/1960 | Howell | 128/418 |
| 3,387,608 | 6/1968 | Figar | 128/2.06 |
| 3,716,059 | 2/1973 | Welborn et al. | 128/419 D |
| 3,857,398 | 12/1974 | Rubin | 128/419 |
| 4,034,150 | 7/1977 | Burnett, III | 174/69 |
| 4,233,987 | 11/1980 | Feingold | 128/639 |
| 4,328,814 | 5/1982 | Arkans | 128/640 |
| 4,365,634 | 12/1982 | Bare et al. | 128/640 |
| 4,391,278 | 7/1983 | Calahan et al. | 128/640 |
| 4,577,639 | 3/1986 | Simon et al. | 128/709 |
| 4,583,549 | 4/1986 | Manoli | 128/640 |
| 4,685,466 | 8/1987 | Rau | 128/639 |
| 4,733,670 | 3/1988 | Hays et al. | 128/693 |
| 4,763,660 | 8/1988 | Kroll et al. | 128/640 |
| 4,852,571 | 8/1989 | Gadsby et al. | 128/640 |
| 4,854,323 | 8/1989 | Rubin et al. | 128/644 |
| 4,957,109 | 9/1990 | Groeger et al. | 128/640 |

Primary Examiner—Lee S. Cohen
Assistant Examiner—Brian Casler
Attorney, Agent, or Firm—Michael, Best & Friedrich

[57] ABSTRACT

A method of monitoring natural electrical impulses from a patient's heart, and providing appropriate therapeutic electrical impulses to a patient's heart comprising the steps of placing on the patient's chest an electrode pad having a plurality of electrode sites arranged such that at least one electrode site is disposed sufficiently near the patient's right arm to intercept an adequate right arm signal, at least one electrode site is disposed sufficiently near the patient's left arm to intercept an adequate left arm signal, and a plurality of additional electrode sites disposed approximately therebetween. The method also includes the steps of measuring voltage differences between pairs and combinations of the electrode sites for providing ECG signals, monitoring the ECG signals, determining if cardiac pacing is required, determining whether atrial or ventricle pacing is most efficacious and providing pacing signals to the favored electrodes, connecting a proper combination of the remaining electrodes to provide an optimal return path for the pacing signal, providing an appropriate defibrillation current through a first plurality of the electrode sites if the ECG signals indicate defibrillation is required, and coupling a second plurality of electrode sites to provide a return path for the defibrillation current.

15 Claims, 4 Drawing Sheets

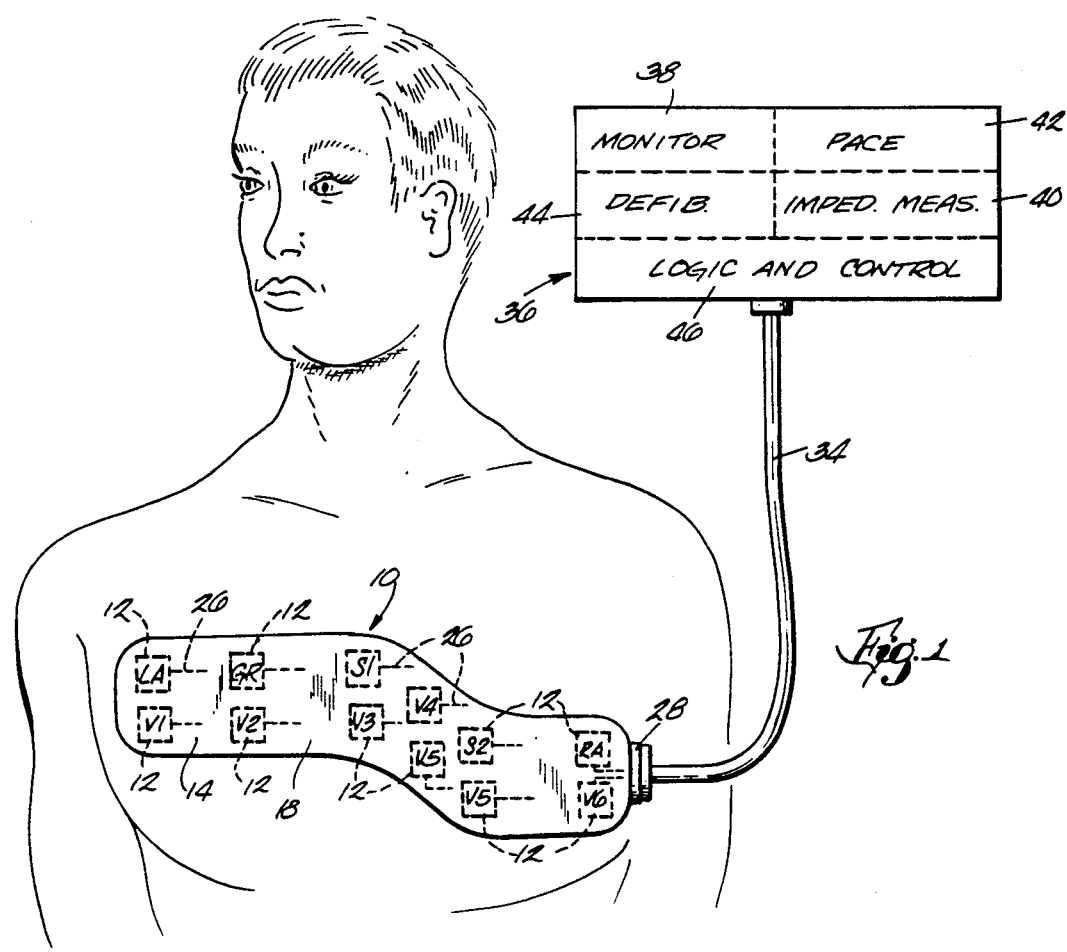

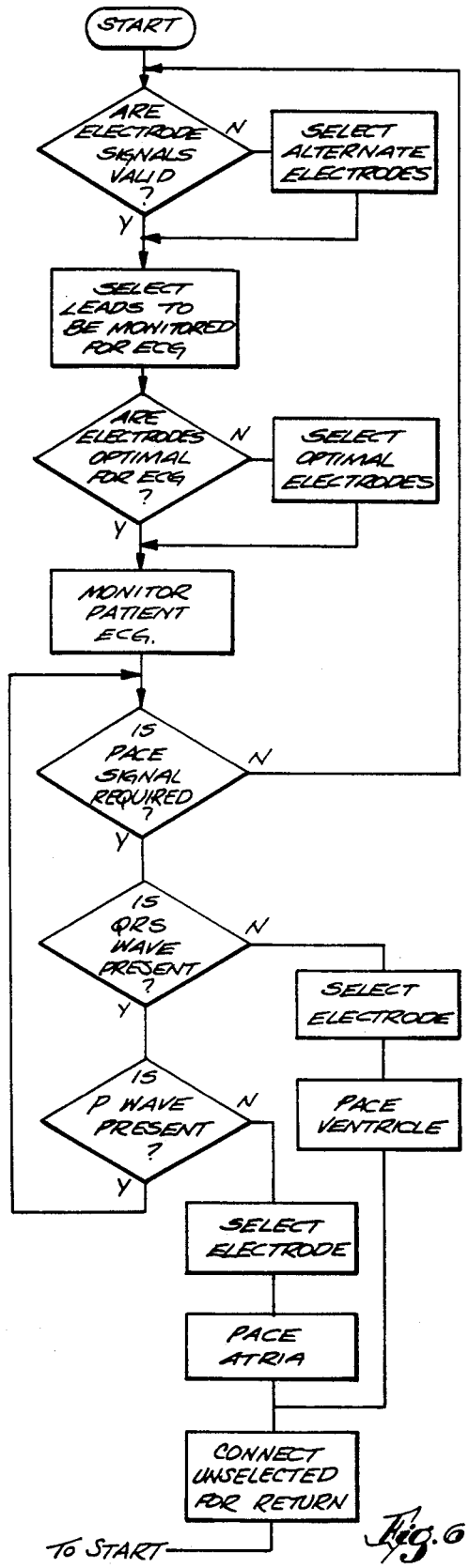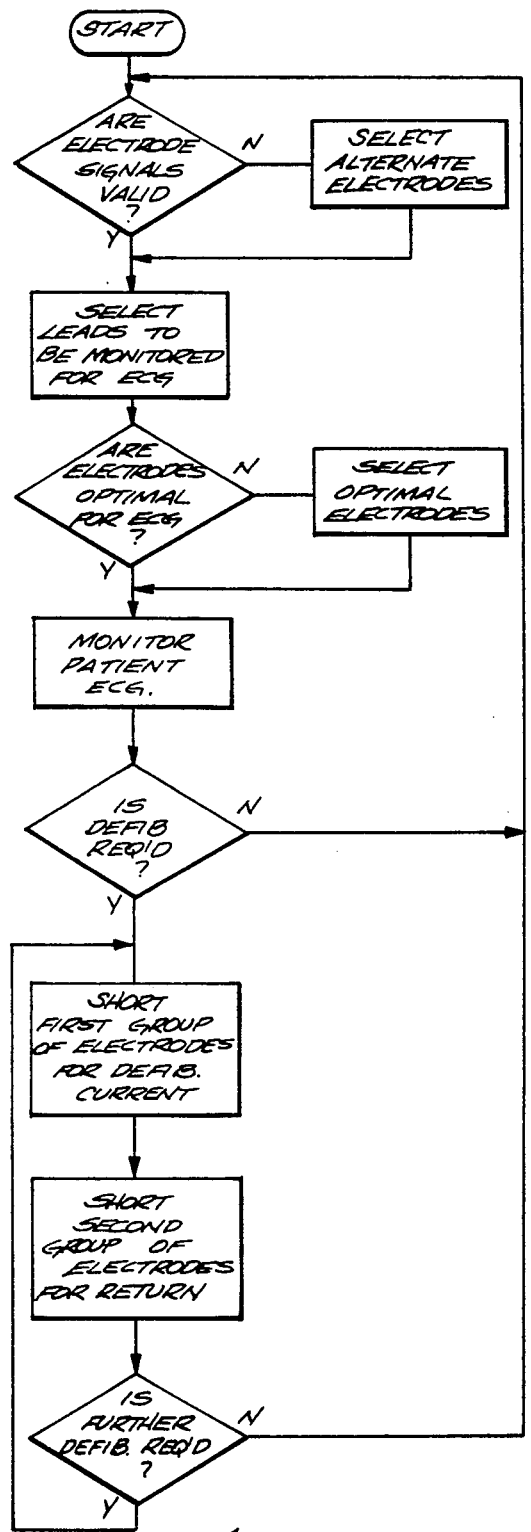

METHOD OF USING A MULTIPLE ELECTRODE PAD ASSEMBLY

BACKGROUND OF THE INVENTION

This invention relates to cardiac electrodes and more particularly to a multiple electrode pad for placement in contact with a patient's skin for receiving and transmitting electrical signals and methods for using the same.

Body surface electrodes are normally employed for non-invasively coupling a patient's intrinsic cardiac electrical activity with various medical diagnostic and therapeutic equipment. Electrical signals generated by the human heart appear in a characteristic pattern throughout the body and on its surface. Such intrinsic cardiac electrical activity may be measured by placing electrodes on the skin of the individual and measuring the voltage between a particular electrode and a reference potential or between selected bipolar pairs of electrodes. Well known bipolar pairs are typically located on patient's right arm (RA), left arm (LA), right leg (RL) (commonly used as a reference), and left leg (LL). Monopolar electrodes referenced properly are referred to as V leads and are positioned anatomically on a patient's chest according to an established convention. In heart monitoring and diagnosis, the voltage differential appearing between two such electrodes or between one electrode and the average of a group of other electrodes represents a particular perspective of the heart's electrical activity and is generally referred to as the ECG. Particular combinations of electrodes are called leads. For example, the leads which may be employed in a twelve lead system are:

$$\text{Lead } I = (LA - RA)$$
$$\text{Lead } II = (LL - RA)$$
$$\text{Lead } III = (LL - LA)$$
$$\text{Lead } V1 = V1 - (LA + RA + RL)/3$$
$$\text{Lead } V2 = V2 - (LA + RA + RL)/3$$
$$\text{Lead } V3 = V3 - (LA + RA + RL)/3$$
$$\text{Lead } V4 = V4 - (LA + RA + RL)/3$$
$$\text{Lead } V5 = V5 - (LA + RA + RL)/3$$
$$\text{Lead } V6 = V6 - (LA + RA + RL)/3$$
$$\text{LEAD } AVL = (LA + RA)/2 - LL$$
$$\text{LEAD } AVF = (LA + LL)/2 - RA$$
$$\text{LEAD } AVR = (RA + LL)/2 - LA$$

In one application, electrical signals produced by the heart are transferred by electrodes to a monitoring apparatus known as an electrocardiograph for further processing. In using electrodes to monitor the heart's electrical activity, it is important that the electrodes be positioned at the conventional anatomical positions to insure the acquisition of signals which will have universal diagnostic meaning. If electrodes are not positioned properly or if they do not make good contact with the patient's skin, the recorded data may be invalid.

While prior art ECG monitoring and diagnostic devices are capable of detecting failed electrodes, their response is to disconnect the failed electrode and substitute another electrode which is valid. While this relieved the problem of invalid data, it resulted in a reduction in the total data which is available. For example, while U.S. Pat. No. 4,577,639 discloses a system wherein a plurality of electrodes are connected, ECG data from only a single electrode pair is utilized. Should one electrode of the utilized pair fail, an unused electrode is substituted. Thus, for example, if Lead II (LL - RA) is being utilized and the RA electrode fails, the device would substitute another electrode, such as LA, to provide Lead III (LL - LA). However, this system was not wholly satisfactory because it did not permit several leads to be monitored simultaneously. Another prior art monitor is disclosed in U.S. Pat. No. 5,022,404 to comprise a system wherein failed electrodes are also disconnected, but this, too, can limit the number of leads being monitored.

Surface chest electrodes can also be used both diagnostically and therapeutically to transmit externally-generated electrical signals transcutaneously to a patient's heart. For example, cardiac impedance measuring, cardiac mapping, pacing and defibrillation are all medical procedures that utilize electrodes in this manner. Impedance measuring is a diagnostic procedure which measures cardiac output and detects mechanical events during a heartbeat, conveying information as to how well a patient's heart is pumping blood. For this procedure, an electrical current is passed through a first set of electrodes on a patient's skin in proximity to the heart and the voltage drop is measured across a second set of intervening electrodes. One of the difficulties with using electrodes for impedance measuring is that in order to achieve meaningful results, proper electrode placement is critical. Such proper electrode placement is generally not known in advance and some degree of electrode modification and repositioning is often beneficial to the signal quality.

Many abnormal cardiac conditions escape detection with present ECG monitoring or diagnostic systems which employ up to twelve leads. Cardiac spacial mapping enhances the probability that such conditions will be detected and is a procedure in which a multiplicity of voltage readings are made simultaneously from a large number of different sites on the patient's chest.

Another procedure that utilizes electrodes to send electrical signals across the patient's skin is external heart pacing. During a pacing procedure, an electrical current is applied transcutaneously to initiate a rhythmic pumping operation in the heart. The present practice of heart pacing is to place two large electrodes on the patient's chest and transcutaneously apply an electrical current without any specific concentration on the most sensitive portions of the heart.

Defibrillation is a medical procedure in which a relatively large electrical current is applied to a patient's heart that has temporarily ceased to function due to a chaotic electrical condition. For this purpose, it is necessary to provide two large contact areas for electrical current to enter and exit the patient's body.

Multiple electrode pads have been disclosed for the purpose of facilitating the simultaneous placement of a plurality of electrodes upon a patient's skin. One example of a prior art electrode pad is disclosed in U.S. Pat. No. 4,583,549. This ECG electrode pad utilizes six electrodes which are positioned on a patient's chest to correspond with an anatomically correct placement for precordial ECG electrodes. Another example is disclosed in U.S. Pat. No. 4,233,987, to comprise a curved strip with a plurality of electrodes arranged in curvilinear relation to one another for monitoring a patient's heart. A further example is illustrated in U.S. Pat. No. 4,763,660, which discloses a plurality of electrodes affixed to an elongated body structure for receiving and transmitting electrical signals to and from a patient.

These and other prior art electrode pads are not wholly satisfactory because even though they can be positioned relatively rapidly, there is no assurance that they would be accurately positioned in the stress of an emergency. Furthermore, prior art electrode pads were normally dedicated to a specific medical, diagnostic or therapeutic procedure, such as ECG monitoring, impedance measuring, pacing or defibrillation.

SUMMARY OF THE INVENTION

It is an object of the invention to provide a new and improved electrode pad having a multiplicity of electrode sites for use in patient monitoring, diagnosis and therapeutic purposes.

Another object of the invention is to provide a new and improved method of defibrillation.

A further object of the invention is to provide a new and improved method of providing patients with a pacemaker signal.

Yet another object of the invention is to provide a new and improved method of patient monitoring.

These and other objects and advantages of the invention will become more apparent from the detailed description thereof taken with the accompanying drawings.

According to one of its aspects, the invention comprises an electrode assembly comprising a flexible, non-conductive base structure which is generally planar and is adapted to conform to the curvature of the patient's chest. The base structure has a contact surface on one side thereof, a plurality of electrodes mounted on the contact surface in a spaced apart relation wherein the base structure supports and electrically insulates the electrodes one from the other, the electrodes being arranged in rows with a plurality of electrodes being disposed in each row. An adhesive is disposed on the contact surface of the base structure in surrounding relation to the electrodes for releasably adhering the electrode assembly to the patient's chest and holding the electrodes in contact therewith.

According to another of its aspects, the invention comprises a method of monitoring and providing therapeutic electrical impulses to a patient's heart, comprising the steps of placing on the patient's chest an electrode assembly having a plurality of electrodes arranged such that at least one electrode is disposed near the patient's right arm and at least another electrode is disposed near the patient's left arm, and a plurality of electrodes are disposed therebetween, measuring voltage differences between pairs of the electrodes for providing electrode lead pair ECG signals, monitoring the ECG signals, determining whether pacing is required, and providing a pace signal to the appropriate electrodes if pacing is required and connecting a plurality of other electrodes to provide an optimal return path for the pace signal, determined from the ECG signals whether defibrillation is required, providing a defibrillation current through a first plurality of the electrodes if defibrillation is required and coupling a second plurality of electrodes to provide a return path for the defibrillation current, at least some of the same electrodes being employed for ECG monitoring, pacing and defibrillation.

According to another of its aspects, the invention comprises a method of monitoring and providing therapeutic electrical impulses to a patient's heart, comprising the steps of placing on the patient's chest an electrode assembly having a plurality of electrodes arranged such that at least a first electrode is disposed in the proximity of the patient's right arm, a second electrode is disposed in the proximity of the patient's left arm, and a third group of electrodes are disposed therebetween and located on the patient's chest, measuring voltage differences between pairs of said electrodes for providing electrode lead pair ECG signals, monitoring said ECG signals, determining from said ECG signals whether defibrillation is required, providing a defibrillation current through a first plurality of said electrodes if defibrillation is required and coupling a second plurality of electrodes to provide a return path for the defibrillation current.

According to another of its aspects, the invention comprises a method of monitoring and providing therapeutic electrical impulses to a patient's heart, comprising the steps of placing on the patient's chest an electrode assembly having a plurality of electrodes arranged such that at least a first electrode is disposed in the proximity of the patient's right arm, a second electrode is disposed in the proximity of the patient's left arm, and a group of electrodes are disposed therebetween and located on the patient's chest, measuring voltage differences between pairs of the electrodes for providing electrode lead pair ECG signals, monitoring the ECG signals, determining whether cardiac pacing is required, connecting at least a first electrode of the plurality of electrodes as a source for the pace signal and at least a second electrode of the plurality of electrodes as a return path for the pace signal, at least one of the first and second electrodes used to provide said pace signal and which define a return path therefor also being used to monitor the ECG signals.

According to another of its aspects, the invention comprises a method of monitoring a patient's heart, comprising the steps of placing on the patient's chest an electrode assembly having a plurality of electrodes such that at least a first electrode is disposed adjacent the patient's right arm, a second electrode is disposed adjacent the patient's left arm a first plurality of electrodes are disposed between the first and second electrodes and located on the patient's chest, and a second plurality of redundant electrodes are located respectively adjacent to the first and second electrodes and the electrodes of the first plurality of electrodes. The method further includes coupling to an ECG monitor pairs of electrodes selected from the first electrode, said second electrode and at least some of the electrodes of the first plurality of electrodes for sensing electrode lead pair ECG signals, monitoring the ECG signals, determining whether any of the first or second electrodes or any of the first plurality of electrodes are providing an invalid signal, uncoupling from the monitor any of the electrodes which are providing an invalid signal and coupling one of the redundant second plurality of electrodes to the monitor whereby monitoring of the patient's heart may continue without significant reduction in the lead pair signal data.

According to another of its aspects, the invention comprises a method of providing therapeutic electrical impulses to a patient's heart, comprising the steps of placing on the patient's chest an electrode assembly having a plurality of individual electrodes spaced apart and electrically isolated, determining whether defibrillation is required, providing a defibrillation current through a first plurality of the electrodes if defibrillation is required, providing a return path for the defibrillation current through a second plurality of electrodes so that the defibrillation current is distributed through the electrodes of the first plurality and said return current is distributed through the electrodes of the second plurality whereby the density of the defibrillation current flowing through the patient's skin is reduced less than that which occurs from single electrodes of the same surface area.

According to another aspect, the invention comprises an electrode assembly for use in providing a defibrillation current to a patient's heart, said assembly comprising a flexible, non-conducting base structure which is generally planar and conforms to the curvature of the patient's chest, said base structure having a contact surface on one side thereof, a plurality of electrodes mounted on the contact surface of the base structure in a spaced apart relation, the base structure supporting and electrically insulating the electrodes one from the other, an adhesive disposed on the contact surface of the base structure in surrounding relation to the electrodes for releasably adhering said electrode assembly to the patient's chest and holding said electrodes in contact therewith, a first plurality of electrodes being connected in parallel to each other for providing said defibrillation current to the patient, and a second plurality of the electrodes being connected in parallel with each other and electrically insulated from the first plurality of electrodes for providing a return path for said defibrillation current.

BRIEF DESCRIPTION OF THE DRAWINGS

FIG. 1 is a frontal view of an electrode pad according to the invention positioned on a patient's chest;

FIG. 2 is a bottom view of an alternate embodiment of the invention;

FIG. 3 is a bottom view of a further embodiment of the invention;

FIG. 4 is a view taken along lines 4-4 of FIG. 3;

FIGS. 6, 7 and 8 are flow diagrams illustrating alternate embodiments of the method according to the invention.

DETAILED DESCRIPTION OF THE PREFERRED EMBODIMENT

Figure 5:
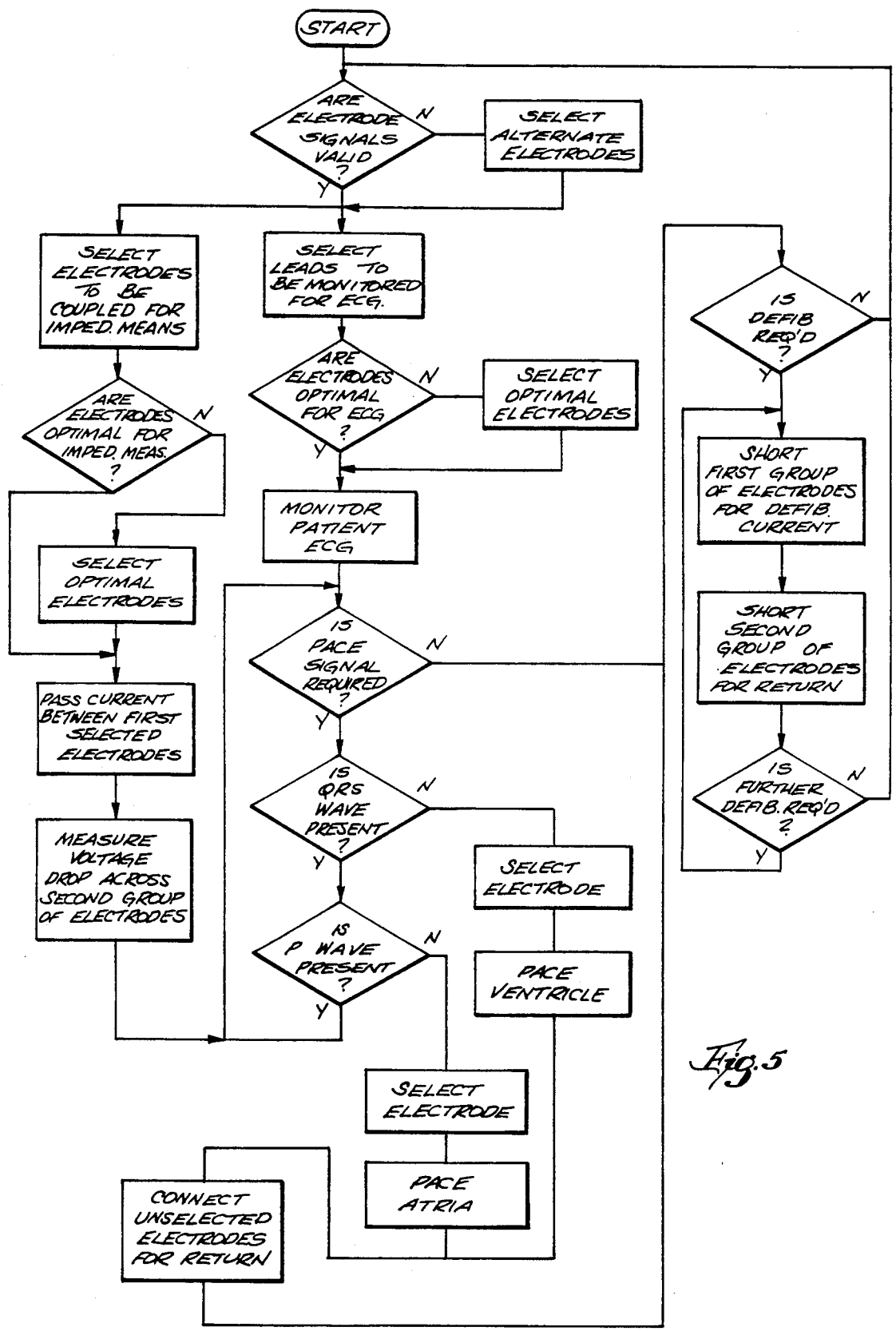
FIG. 5 is a flow diagram illustrating the method according to the invention.

The electrode assembly 10 according to the invention includes a pad 11 and a plurality of groups of electrodes 12. In the first embodiment of the invention shown in FIG. 1 there are six groups of electrodes 12 with the groups being arranged in rows of two electrodes each. The electrodes 12 are labeled from left to right and from top to bottom in each row as LA (left arm), V1, GRND (ground), V2, S1 (spare), V3, V4, LL (left leg), S2 (spare), V5, RA (right arm), and V6.

The pad 11 is composed of a conventional, flexible foam insulating material, such as Mylar or polyester. Electrodes 12 each comprise a layer of conductive material, such as copper or tin, which is applied to one surface of the pad 11. For example, the electrodes may comprise a metallic foil or may be applied to the foam pad 10 by a printing process. Electrodes 12 are spaced apart with the pad material providing electrical insulation therebetween. While each of the electrodes 12 are shown in the drawings to be rectangular, they may have any shape which augments construction and/or optimizes the electrical field characteristics.

A layer of a conventional, non-conductive adhesive material covers the contact surface of the pad in surrounding relation to the electrodes 12 for holding the pad in contact with the patient's skin. Also, a well-known conductive gel or polymer is disposed on the exposed surface of each electrode 12 to provide electrical contact with the patient. A protective separation paper covers the pad's entire contact surface in storage and prior to use to mask the adhesive.

The pad 11 is configured so that the contacts 12 will be positioned in the desired body locations and so that it conforms to the curvatures of the patient's chest when in use. In the preferred embodiment, the pad 11 has a first horizontally extending section 14 at one end and a second horizontally extending section 16 at the other end. The axes of the sections 14 and 16 are generally parallel. Between the sections 14 and 16, there is an obliquely extending transition section 18. The first two rows of electrodes 12 are located in the first section 14, the third row is located in the transition section 18, and the last three rows are located in the second section 16.

A conductor 26 is connected to each of the electrodes 12 and is embedded in the pad 11 and each is electrically insulated by the pad from the other conductors. Each of the conductors 26 extends from its respective electrode to a terminal 28 located at one end of the electrode pad. A suitable cable 34 having a mating terminal 35 electrically connects the electrodes 12 to monitoring, diagnostic, and signal generating apparatus 36. More particularly, the apparatus 36 may comprise a conventional heart monitoring and emergency care device which includes an ECG monitor 38, a multi-lead ECG analysis system 39, a heart impedance measuring system 40, a pacemaker signal generating system 42, a defibrillator 44 and a logic and control system 46. One such apparatus is the Model 1500 Advisory Defibrillator manufactured by Marquette Electronics, Inc. The system may also include a cardiac mapping system 47.

In use, the electrode assembly 10 is preferably positioned with the LA electrode located near the patient's left arm and the RA electrode positioned adjacent the patient's right arm, with the remaining electrodes positioned across the chest and between the LA and RA electrodes. "Adjacent" in this context is intended to mean positioned so that the signal is electrically similar to the signal obtained by actually positioning the electrode on the appropriate arm or leg. Two of the V electrodes can be considered as providing signals electrically similar to the LL and RL leads. The pad is pressed against the patient's chest to provide good adhesion and electrical contact. As illustrated in FIG. 5, for ECG monitoring, the logic and control 46 selects which of the ECG leads will be monitored. The spare electrodes S1 and S2 provide a redundancy so that the desired monitoring signals can be generated notwithstanding possible bad electrode connections and malpositioning on the patient's skin. For example, if leads II, III and V are to be monitored, voltage signals from electrodes LL, RA, LA and one or more of the V leads is selected. The logic and control system 46 determines whether the connections from these electrodes have proper contact with the patient's skin. Furthermore, from signal strength and quality, system 46 selects those electrodes which are in good electrical contact and positioned to provide the most optimal signals. For example, lead V1 may be employed in place of the right arm, V6 may be employed in place of the left arm electrode, one of the electrodes V3 or V5 may be employed for the left leg electrode or one of the electrodes V1, V2, V3, V4, V5, S1 or S2 may be employed as the V electrodes. If any pair of electrodes in the same row or adjacent rows straddle an optimum electrode position, the logic and control system 46 may be programmed to provide a weighted signal average to the ECG monitor as though a single intermediate electrode was optimally positioned. Because of the availability of redundant electrodes, the quantity of data available to the apparatus 36 is not diminished even though there may be one or a few bad electrodes.

For impedance measuring, electric current is introduced transcutaneously to the patient through an outer pair of electrodes, that is, electrodes LA, V1, GRND or V2, or electrodes S2, V5, RA and V6. The logic and control system 46 and the impedance measuring system 47 then measure the voltage drop across, a pair of inner electrodes, i.e., electrodes S1, V3, V4 or V5, or if electrodes LA, V1, RA and V6 are employed, impedance measurements can be taken across any pair of interior electrodes. Because the impedance of the heart changes as it fills with and discharges blood, impedance measurement provides an indication of heart activity. The logic and control system 46 and the impedance measuring system 40 select the pairs of inner and outer electrodes which provide the best impedance measuring results. By selecting various pairs of electrodes for this purpose, the effect of false signals due to artifacts and the like can be minimized.

If the logic and control system 46 determines from the monitored signals that it is necessary to provide the patient with a pace signal, the logic and control system 46 commands the pacing circuit 42 to supply the pacing signal through the appropriate electrodes. For example, if the monitor senses the absence of the QRS wave, the pace signal will be provided to the electrode most favorably positioned to pace the ventricle. If the monitor senses the absence of a P wave, but the QRS wave is present, the pace signal will be provided to the electrode most favorably positioned to pace the atria. In this manner, the logic and control system 46 determines which of the electrodes 12 are preferentially positioned for delivering the pacing signal to the correct heart location. The return path for the pace signal is through the remaining electrodes. This insures that there is the desired unbalanced electric field which is strongest in the selected area of the heart being paced and weaker elsewhere.

If the logic and control system 46 determines that defibrillation is required, it commands the defibrillator 44 to internally connect in parallel a first group or cluster of electrodes 12 at one end of the pad 11 for the delivery of a defibrillating current and a second group or cluster of electrodes at the other end of the pad are also connected in parallel to define a return path. In each case, the requisite number of electrodes are employed to define the required electrode areas for delivery and return of the defibrillation current. Present industry standards dictate that the minimum electrode single surface area should be at least 60 square centimeters for both the delivery and return path of the defibrillating current. However, it has been discovered that defibrillation electrodes are more efficacious and safe when configured in a discontinuous cluster or array than when they compose a solid electrode. It has been found that the defibrillation current is concentrated around the periphery of the electrode in contact with the patient's skin. It is not uncommon for some discoloration and thermal trauma to result from this concentrated current. By providing a plurality of shorted electrodes 12, the defibrillation current is diffused over the periphery of each and, therefore, is less concentrated than in the case of a single large electrode. Furthermore, the diffusion of the current pattern emerging from the cluster if relating electrodes renders the pattern of current in the heart itself to be more homogeneous. This homogeneity improves the efficiency of defibrillation. To adhere to the industry standard a sufficient number electrodes can easily be coupled by the logic and control circuit 46 to provide the requisite surface area. However, if a cluster of electrodes having a greater or lesser total surface area is subsequently accepted, this can be easily accomplished with the attendant benefits. The assembly 10 thus provides the necessary large contact area and the desired uniform field required for defibrillation.

In emergency situations, using prior art apparatus, medical personnel must connect up to ten wires and position up to fifteen electrodes on the patient. This may take up to a minute or more if the wires become entangled. Furthermore, when a large number of electrodes are applied to the patient, it is common for improper contact to occur in at least one or more electrodes. With the electrode assembly 10 in accordance with the invention, a number of redundant electrodes are provided, thereby insuring good electrode contact for a sufficient number of electrodes to enable the successful performance of the various desired procedures. Toward this end, the second embodiment of the invention shown in FIG. 2 comprises an assembly 48 having six columns of electrodes 12 with three electrodes in each column. This increased number of electrodes provides more redundancy, thereby enabling the advisory monitor and defibrillator 36 to scan more electrodes for the optimum selection and employment of electrodes during the various diagnostic and therapeutic procedures. A further embodiment of the invention is shown in FIG. 4 to comprise an assembly 50 having four electrodes 12 in each row. The invention contemplates varying the numbers of columns and electrodes per column for optimizing the number of electrodes and thereby achieving more redundancy and better spatial resolution with respect to the heart's electrical patterns.

In order to accommodate patients having different sized chests, accordion pleats 52 may be provided in the pad 11 between rows of electrodes 12 as shown in FIGS. 3 and 4. These accordion pleats 52 allow the pad 11 to be stretched to accommodate larger chests while the unstretched pad can be applied appropriately to a smaller chest.

While FIGS. 1, 2 and 3 show six rows of electrodes and two, three or four electrodes per row, the invention contemplates greater or lesser numbers of rows and greater numbers of electrodes per row, limited only by space limitations. Thus, the invention includes X rows of electrodes with N electrodes per row, where both X and N are greater than one.

Applications besides those discussed above wherein large numbers of electrodes are desirable are cardiac spacial mapping and multo-lead ECG monitoring. For cardiac mapping, an electrode pad, such as that illustrated in FIG. 3, or one having a greater number of electrodes would provide the requisite number of sites. For multi-lead ECG monitoring, such as twelve-lead monitoring, the electrode of FIG. 3 or one having a greater number of electrodes would provide sufficient redundant electrodes so that all of the leads can be monitored even if one or a few electrodes were loose or not making proper contact.

FIG. 5 illustrates the method in accordance with the preferred embodiment of the invention. The logic and control system 46 first determines whether the electrode signals are valid. If any invalid signals are detected, alternate electrodes are selected. For ECG measurement, the logic and control system 46 selects those valid electrodes which are positioned on the patient's chest to correspond with an anatomically correct placement of precordial ECG electrodes. If the selected electrodes are not optimal, optimal electrodes are selected. After electrode selection, the patient's ECG signals are monitored. If the monitored signals indicate that pacing is required, a pace signal is provided to a favorably positioned electrode and a plurality of unselected electrodes are connected in parallel to provide a return path. If no pacemaker signal is required, or upon the completion of the pacemaker signal, the system determines if defibrillation is required. If so, a first group or cluster of electrodes at one side of the pad 11 are shorted together to provide a path for the defibrillation current and a second group or cluster of electrodes at the other side of the pad 11 are shorted to provide a return path. The number of electrodes chosen is determined by the required surface area, which under present standards is sixty square centimeters. When no defibrillation is required or further defibrillation is not required, the program sequence is repeated.

By providing redundant electrodes positioned adjacent the electrodes selected for ECG measurement, it is possible to internally disconnect any electrode providing an invalid signal with a closely positioned electrode which is valid. In this manner, the electrode leads selected to be monitored, such as Lead I, II, III, V1, V2, V3, V4, V5, V6, AVL, AVF and AVR may be continued instead of deleting a lead or switching to an alternate lead.

As an additional procedure, impedance measuring may be employed. If so, electrodes are selected to be coupled for impedance measuring, in which case, optimum electrodes are chosen. Current is then passed between a first group of selected electrodes adjacent the ends of the electrode pad and a voltage drop is measured across the second group of electrodes.

FIGS. 6 and 7 show alternate embodiments of the invention. In the embodiment of FIG. 6, the logic and control circuit is programmed for ECG monitoring and pacing only, while in the embodiment of FIG. 7, the logic and control circuit is programmed for ECG monitoring and defibrillation only.

The invention also contemplates the concept of an electrode pad for defibrillation only and including a first cluster of electrodes at one side and connected in parallel for the delivery of defibrillation current and a second cluster of electrodes at the other side and connected in parallel. Because defibrillation current flows around the periphery of the electrodes, the density of the current flowing through the patient's skin can be reduced by delivering the defibrillation current through a cluster of separate, electrically isolated electrodes instead of a single electrode. Thus, the threshold of effective defibrillation can be achieved with less patient trauma than with a single electrode having a similar surface area. Also, because separate electrodes of the same surface area have a greater total periphery than a single electrode of the same area, effective defibrillation can be achieved with a cluster of electrodes having a smaller total surface area.

Figure 8:
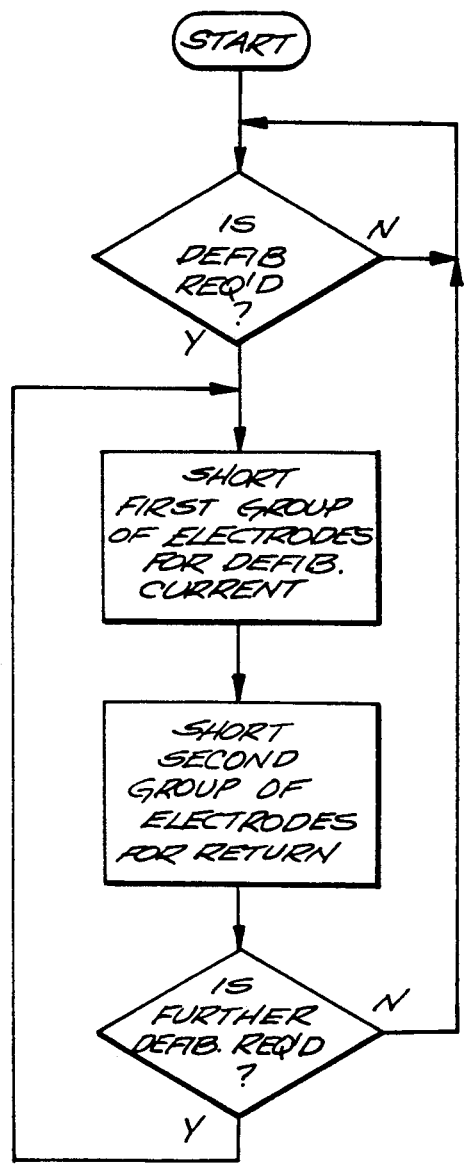

FIG. 8 shows a further embodiment of the invention wherein the logic and control circuit is programmed as a defibrillator. In this embodiment of the invention, the electrodes 12 in any of the pads shown in FIGS. 1, 2 and 3 are internally connected so that a first group of electrodes are connected in parallel for the delivery of defibrillation current and a second plurality of electrodes are connected in parallel to provide a return path.

While only a few embodiments of the invention have been illustrated and described, it is not intended that the invention be limited thereby, but only by the scope of the appended claims.

We claim:

1. A method of monitoring and providing therapeutic electrical impulses to a patient's heart, comprising the steps of placing on the patient's chest an electrode assembly having a plurality of electrodes arranged such that at least a first electrode is disposed adjacent the patient's right arm, at least a second electrode is disposed adjacent the patient's left arm, and a third group of electrodes are disposed therebetween and located on the patient's chest, measuring voltage differences between pairs of said electrodes for providing electrode lead pair ECG signals, monitoring said ECG signals, said pairs defining a first electrode array, determining whether cardiac pacing is required, providing a pace signal and a return path for the pace signal through a second plurality of said electrodes defining a second electrode array if a pace signal is required, determining from said ECG signals whether defibrillation is required, providing a defibrillation current through a third plurality of said electrodes defining a third electrode array if defibrillation is required and coupling a fourth plurality of said electrodes in a fourth array to provide a return path for the defibrillation current, each of said first, second, third and fourth electrode arrays including at least some electrodes in common in another one of said arrays, but all of said arrays not including the same electrodes whereby each array of electrodes may be optimally chosen for performing its specific function from the plurality of electrodes.

2. The method set forth in claim 1 and including providing and returning said defibrillation current over a distributed area of said third and fourth arrays of electrodes having at least 60 square cm.

3. The method set forth in claim 1 wherein the electrode assembly includes a pad for supporting the electrodes and having opposite ends, at least one electrode being disposed adjacent each end of the pad and a plurality of electrodes being disposed therebetween, and providing electric current between at least two electrodes adjacent the ends of said electrode assembly and measuring the voltage drop between a different pair of electrodes disposed therebetween for measuring the impedance of the patient's heart between said at least two electrodes and a different pair of electrodes, said at least two electrodes also being a part of the electrodes forming at least one of said first, second, third or fourth arrays.

4. The method set forth in claim 3 and including the step of coupling leads to at least some of said electrodes, measuring voltage signals on said leads for deriving said lead pair ECG signals, providing said ECG signals to an ECG monitor, said monitor having the capability of distinguishing between valid and invalid lead pair ECG signals, determining if any of the lead pair ECG signals are invalid signals and uncoupling any such lead from the ECG monitor and coupling to said monitor a lead connected to another electrode.

5. The method set forth in claim 4 wherein the electrode assembly includes a pad for supporting the electrodes and having opposite ends, at least one electrode being disposed adjacent each end of the pad and a plurality of electrodes being disposed therebetween, and providing electric current between at least two electrodes adjacent the ends of said electrode assembly and measuring the voltage drop between a different pair of electrodes disposed therebetween for measuring the impedance of the patient's heart, said at least two electrodes also being a part of the electrodes forming at least one of said first, second, third or fourth arrays.

6. The method set forth in claim 5 and including providing and returning said defibrillation current over a distributed area of said third and fourth arrays of electrodes having at least 60 square cm.

7. The method set forth in claim 1 and including the step of coupling leads to at least some of said electrodes, measuring voltage signals on said electrodes for deriving said lead pair ECG signals, providing said ECG signals to an ECG monitor, said monitor having the capability of distinguishing between valid and invalid lead pair ECG signals, determining if any of the lead pair ECG signals are invalid signals and uncoupling any such lead from the ECG monitor and coupling to said monitor a lead connected to another electrode.

8. The method set forth in claim 1 and including the step of determining which pairs of electrodes provide optimal ECG lead pair signals and monitoring the ECG lead pair signals from said electrodes.

9. A method of monitoring and providing therapeutic electrical impulses to a patient's heart, comprising the steps of placing on the patient's chest an electrode assembly having a plurality of electrodes arranged such that at least a first electrode is disposed adjacent the patient's right arm, at least a second electrode is disposed adjacent the patient's left arm, and a third group of electrodes are disposed therebetween and located on the patient's chest, measuring voltage differences between pairs of said electrodes defining a first plurality of said electrodes for providing electrode lead pair ECG signals, monitoring said ECG signals, determining from said ECG signals whether defibrillation is required, providing a defibrillation current through a second plurality of said electrodes if defibrillation is required and coupling a third plurality of electrodes to provide a return path for the defibrillation current, the second and third pluralities of electrodes each including at least some of the electrodes of the first plurality of electrodes so that the electrodes for ECG measurment and defibrillation may be optimally chosen.

10. A method of monitoring and providing therapeutic electrical impulses to a patient's heart, comprising the steps of placing on the patient's chest an electrode assembly having a plurality of electrodes arranged such that at least a first electrode is disposed adjacent the patient's right arm, a second electrode is disposed adjacent the patient's left arm, and a third group of electrodes are disposed therebetween and located on the patient's chest, measuring voltage differences between pairs of said electrodes for providing electrode lead pair ECG signals, monitoring said ECG signals, determining whether cardiac pacing is required, providing a pace signal to at least a first electrode of the plurality of electrodes and connecting at least a second electrode of the plurality of electrodes as a return path for the pace signal, at least one of the first and second electrodes through which said pace signal is provided and which define a return path therefor also being used to monitor the ECG signals so that the electrodes for ECG measurement and pacing may be optimally chosen.

11. The method set forth in claim 10 and including the steps of connecting a plurality of said electrodes to provide a return path for the pace signal, at lease some of the electrodes through which said pace signal is provided and which define a return path therefor are the same as at least some of those between which the ECG signals are measured.

12. A method of monitoring a patient's heart, comprising the steps of placing on the patient's chest an electrode assembly having a plurality of electrodes such that at least a first electrode is disposed adjacent the patient's right arm, a second electrode is disposed adjacent the patient's left arm, a first plurality of electrodes are disposed therebetween and located on the patient's chest, and a second plurality of redundant electrodes are located respectively adjacent said first and second electrodes and the electrodes of the first plurality, coupling to an ECG monitor pairs of electrodes selected from said first electrode, said second electrode and the electrodes of said first plurality of electrodes for sensing a plurality of specific electrode lead pair ECG signals, monitoring said ECG signals, determining whether any of the first or second electrodes or any of said first plurality of electrodes are providing an invalid signal, uncoupling from said monitor any of said electrodes which are providing an invalid signal and coupling one of the redundant second plurality of electrodes to said monitor whereby monitoring of the patient's heart may continue with the measurement of the plurality of specific lead pair ECG signals.

13. A method of providing therapeutic electrical impulses to a patient's heart, comprising the steps of placing on the patient's chest an electrode assembly having a first and second plurality of individual electrodes spaced apart and electrically isolated from each other, said first and second plurality of electrodes having a first and second total contact area, respectively, determining whether defibrillation is required, providing a defibrillation current through said first plurality of electrodes if defibrillation is required, providing a return path for the defibrillation current through said second plurality of electrodes so that said defibrillation current is distributed through the electrodes of the first plurality and said return current is distributed through the electrodes of the second plurality whereby the density of the defibrillation current flowing through the patient's skin is less than that which would occur if the same current were passed through single electrodes having the same surface area as the first total contact area.

14. A method of monitoring and providing therapeutic electrical impulses to a patient's heart, comprising the steps of placing on the patient's chest an electrode assembly having a plurality of electrodes arranged such that at least a first electrode is disposed adjacent the patient's right arm, a second electrode is disposed adjacent the patient's left arm, and a third group of electrodes are disposed therebetween and located on the patient's chest, connecting selected pairs of electrodes to an ECG monitor, measuring voltage differences between said pairs of electrodes for providing electrode lead pair ECG signals, monitoring said ECG signals, determining whether a pace signal is required, providing a pace signal to one of the plurality of electrodes if the requirement for a pace signal is determined, connecting a group of other electrodes to provide a return path for the pace signal, determining from said ECG signals whether defibrillation is required, providing a defibrillation current in parallel through a first plurality of said electrodes if defibrillation is required and coupling a second plurality of electrodes in parallel to provide a return path for the defibrillation current.

15. A method of monitoring a patient's heart, comprising the steps of placing on the patient's chest an electrode assembly having a plurality of electrodes arranged such that at least a first electrode is disposed adjacent the patient's right arm, at least a second electrode is disposed adjacent the patient's left arm, and a group of electrodes are disposed therebetween and located on the patient's chest, determining which selected pairs of electrodes of said plurality of electrodes provide optimal ECG signals, measuring voltage differences between at least three selected pairs of electrodes or between one of said electrodes and the average of other electrodes for providing electrode lead pair ECG signals, at least some of the plurality of other electrodes being redundant, monitoring said ECG lead pair signals, determining whether the voltage signal in any of the electrodes comprising said selected electrode pairs is providing an invalid signal and switching to an adjacent redundant electrode from the invalid electrode to maintain substantially the same lead pair.

* * * * *

UNITED STATES PATENT AND TRADEMARK OFFICE
CERTIFICATE OF CORRECTION

PATENT NO. : 5,184,620

DATED : February 9, 1993

INVENTOR(S) : Michael J. Cudahy and Robert A. Stratbucker

It is certified that error appears in the above-identified patent and that said Letters Patent is hereby corrected as shown below:

Column 12, Line 59, Please delete "third group" and insert -- plurality --.

Signed and Sealed this

Seventh Day of December, 1993

Attest:

BRUCE LEHMAN

Attesting Officer     Commissioner of Patents and Trademarks